(12) United States Patent
Biadatti et al.

(10) Patent No.: US 7,439,396 B2
(45) Date of Patent: Oct. 21, 2008

(54) PHARMACEUTICAL/COSMETIC COMPOSITIONS COMPRISING NOVEL LIGANDS THAT ACTIVATE RAR RECEPTORS

(75) Inventors: Thibaud Biadatti, Opio (FR); Anne-Pascale Luzy, Valbonne (FR)

(73) Assignee: Galderma Research & Development, Biot (FR)

( * ) Notice: Subject to any disclaimer, the term of this patent is extended or adjusted under 35 U.S.C. 154(b) by 39 days.

(21) Appl. No.: 11/403,916

(22) Filed: Apr. 14, 2006

(65) Prior Publication Data
US 2007/0004726 A1 Jan. 4, 2007

(30) Foreign Application Priority Data
Oct. 17, 2003 (FR) .................................. 03 12154
Oct. 15, 2004 (FR) ................ PCT/FR2004/002646

(51) Int. Cl.
C07C 241/00 (2006.01)
C07C 243/00 (2006.01)
C07C 249/00 (2006.01)
C07C 251/00 (2006.01)
C07C 259/00 (2006.01)
C07C 291/00 (2006.01)
C07C 229/00 (2006.01)

(52) U.S. Cl. ....................... 564/249; 564/253; 564/256; 562/433

(58) Field of Classification Search .................. 562/433; 564/249, 253, 256
See application file for complete search history.

(56) References Cited

U.S. PATENT DOCUMENTS
5,905,088 A 5/1999 Diaz et al.
6,395,260 B1 5/2002 Ley et al.
2003/0049287 A1 3/2003 Ley et al.

FOREIGN PATENT DOCUMENTS
EP 0 816 352 B1 1/1998
GB 2 246 777 A 2/1992
WO WO 94/15901 A1 7/1994
WO WO 01/43712 A1 6/2001

OTHER PUBLICATIONS
International Search Report corresponding to PCT/FR 2004/002646 issued on Jun. 21, 2005, 8 pages.

*Primary Examiner*—Shaojia Anna Jiang
*Assistant Examiner*—Jennifer Y Cho
(74) *Attorney, Agent, or Firm*—Buchanan, Ingersoll & Rooney, PC

(57) ABSTRACT

Novel ligand compounds that activate RAR receptors have the following structural formula (I):

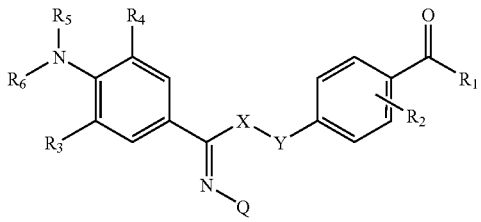

and are suited for formulation into pharmaceutical compositions useful in human or veterinary medicine, or, alternatively, into cosmetic compositions.

21 Claims, 1 Drawing Sheet

PHARMACEUTICAL/COSMETIC COMPOSITIONS COMPRISING NOVEL LIGANDS THAT ACTIVATE RAR RECEPTORS

CROSS-REFERENCE TO PRIORITY/PCT APPLICATIONS

This application claims priority under 35 U.S. § 119 of FR 03/12154, filed Oct. 17, 2003, and is a continuation of PCT/FR 2004/002646, filed Oct. 15, 2004 and designating the United States (published in the French language on Apr. 28, 2005 as WO 2005/037772 A2; the title and abstract were also published in English), each hereby expressly incorporated by reference and each assigned to the assignee hereof.

BACKGROUND OF THE INVENTION

1. Technical Field of the Invention

The present invention relates to novel compounds as novel and useful industrial bioactive agents, which are ligands that activate RAR receptors. This invention also relates to compositions containing the subject novel compounds, namely, pharmaceutical compositions suited for administration in human or veterinary medicine, or alternatively in cosmetic compositions, and also to non-therapeutic applications of these compositions.

2. Description of Background and/or Related and/or Prior Art

Compounds with activity of retinoid type (vitamin A and its derivatives) are widely described in the literature as having activity in cell proliferation and differentiation processes. These properties provide this class of compounds high potential in the treatment or prevention of numerous pathologies, and more particularly in dermatology and cancer. Many biological effects of retinoids are mediated by modulating the nuclear retinoic acid receptors (RAR).

The RAR receptors activate transcription by binding to DNA sequence elements, known as RAR response elements (RARE), in the form of a heterodimer with the retinoid X receptors (known as RXRs).

Three subtypes of human RARs have been identified and described: RARα, RARβ and RARγ.

Chemical compounds with activating activity on receptors of RAR type are known in the prior art. Mention may be made, especially of the aromatic heterocyclic biaryl compounds described in EP-0-816,352 B1, which find applications in the treatment of dermatological, rheumatic, respiratory and ophthalmological complaints or afflictions and also in the cosmetics field.

Nevertheless need continues to exist for novel active agents suited to treat human complaints, conditions or afflictions, especially dermatological afflictions, or to cosmetically enhance the appearance of the skin.

SUMMARY OF THE INVENTION

It has now surprisingly and unexpectedly been determined that certain novel heterocyclic compounds, which are ligands that activate retinoic acid receptors, find applications in human and veterinary medicine, especially in human dermatology, and also in the cosmetics field.

Thus, the present invention features novel compounds having the following structural formula:

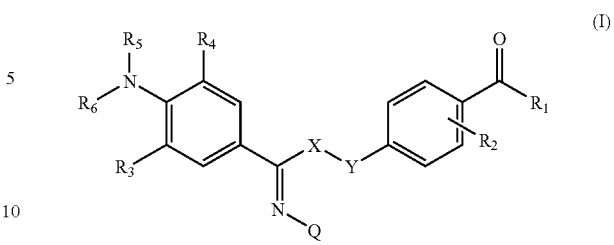

in which:

$R_1$ is an —OH radical, a radical $OR_7$ or a radical —$NR_8R_9$, wherein $R_7$, $R_8$ and $R_9$ are as defined below;

$R_2$ is a hydrogen atom, a fluorine atom, a chlorine atom, an alkyl radical having 1 to 3 carbon atoms, an —OH radical or a radical —$OR_{10}$, wherein $R_{10}$ is as defined below;

$R_3$ is a hydrogen atom, a methyl radical, an ethyl radical, an isopropyl radical, a tert-butyl radical or a —$CF_3$ radical;

$R_4$ is a hydrogen atom, a fluorine atom, a chlorine atom, a radical —$OR_{11}$, a methyl radical, an ethyl radical, an isopropyl radical, a tert-butyl radical or a —$CF_3$ radical, wherein $R_{11}$ is as defined below;

$R_5$ and $R_6$, which may be identical or different, are each a hydrogen atom, a methyl radical, an ethyl radical, an n-propyl radical, an isopropyl radical, a tert-butyl radical, a radical —$COR_{12}$ or may together form, with the nitrogen atom from which they depend, a piperidine, pyrrolidine, morpholine, pyrrolidin-2-one or piperid-2-one heterocycle, which may be unsubstituted or substituted with one or more methyl, ethyl, fluorine or chlorine groups, wherein $R_{12}$ is as defined below;

Q is an —OH radical, a radical —$OR_{13}$, a radical —$NR_{14}R_{15}$ or a radical —$SO_2R_{16}$, wherein $R_{13}$, $R_{14}$, $R_{15}$ and $R_{16}$ are as defined below;

is a divalent radical having one of the following structures:

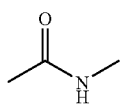 a)

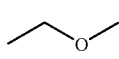 b)

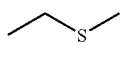 c)

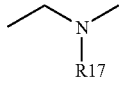 d)

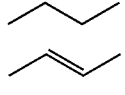 e)

 f)

wherein $R_{17}$ is as defined below;

$R_7$ is a linear or branched alkyl radical having from 1 to 20 carbon atoms, an alkenyl radical, a monohydroxyalkyl radical, a polyhydroxyalkyl radical, an aryl radical, an optionally substituted aralkyl radical or a sugar residue;

R8 and R9, which may be identical or different, are each a hydrogen atom, an —OH radical, an alkyl radical having 1 to 6 carbon atoms, a monohydroxyalkyl radical, a polyhydroxyalkyl radical, an optionally substituted aryl radical, or form with the nitrogen atom from which they depend, an amino acid residue or a peptide residue, or alternatively R8 and R9 may together form, a piperidine, pyrrolidine, morpholine, pyrrolidin-2-one or piperid-2-one heterocycle;

R10 is an alkyl radical having from 1 to 6 carbon atoms;

R11 is an alkyl radical having from 1 to 6 carbon atoms or a mono- or polyether radical;

R12 is an alkyl radical having from 1 to 6 carbon atoms or a radical —OR18, wherein R18 is as defined below;

R13 is a linear or branched alkyl radical having from 1 to 15 carbon atoms;

R14 and R15, which may be identical or different, are each a hydrogen atom, an alkyl radical having from 1 to 6 carbon atoms or a radical —COR19, wherein R19 is as defined below;

R16 is an alkyl radical having from 1 to 6 carbon atoms;

R17 is a hydrogen atom, an alkyl radical having from 1 to 6 carbon atoms or a —CF3 radical;

R18 is an alkyl radical having from 1 to 6 carbon atoms;

R19 is an alkyl radical having from 1 to 6 carbon atoms;

and the salts of the compounds of formula (I) when $R_1$ is an OH function, and also the optical and geometrical isomers of said compounds of formula (I).

When the compounds according to the invention are in the form of a salt, it is preferably a salt of an alkali metal or alkaline earth metal, or, alternatively, a zinc salt or a salt of an organic amine.

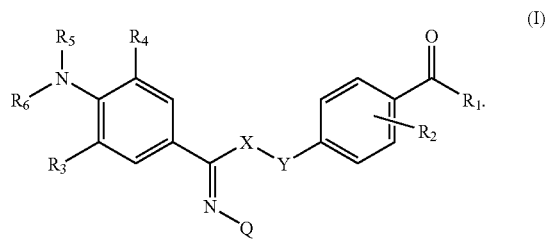

Figure 1:
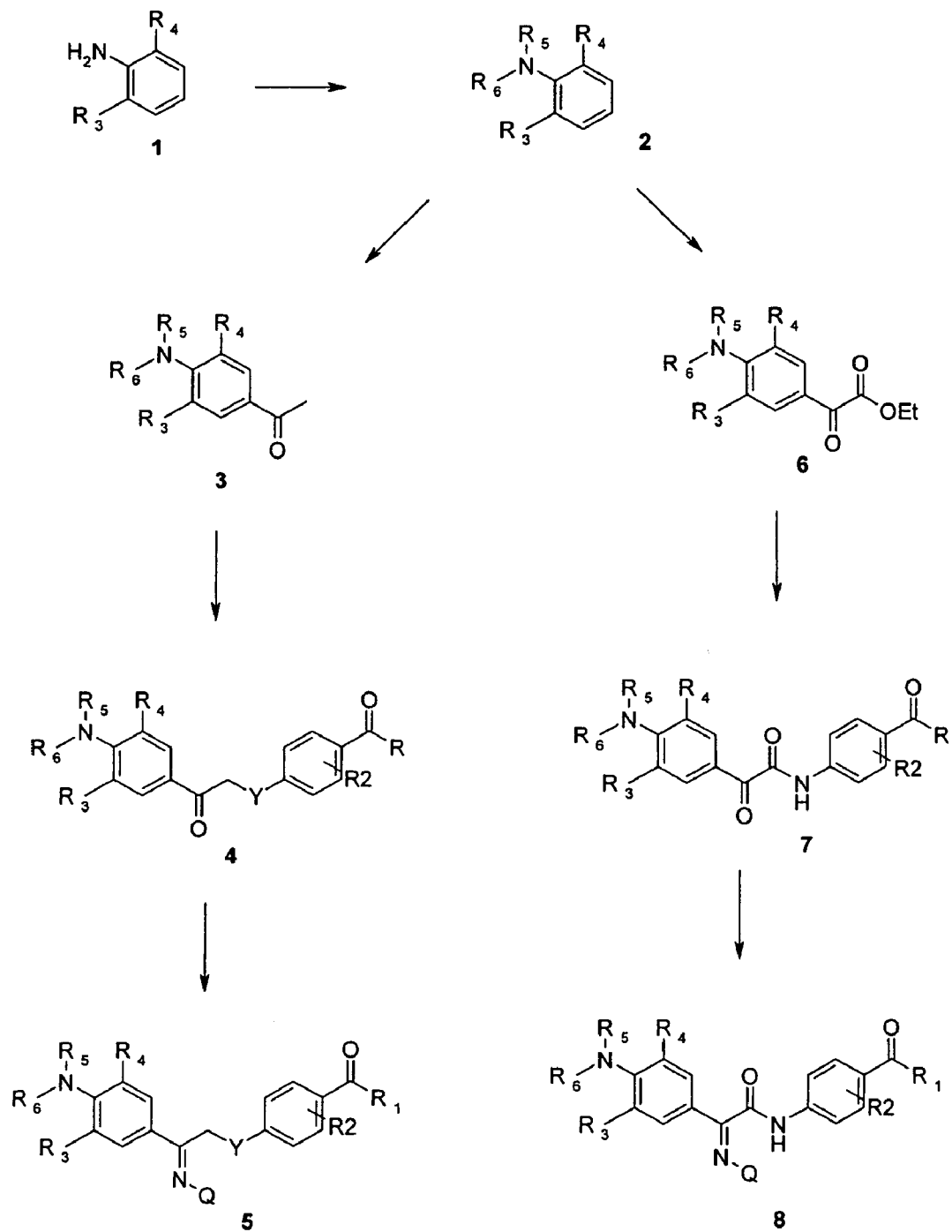
FIG. 1 depicts reaction schemes for preparing the compounds of Formula I below.

DETAILED DESCRIPTION OF BEST MODE
AND SPECIFIC/PREFERRED EMBODIMENTS
OF THE INVENTION

According to the present invention, the term "alkyl having from 1 to 6 carbon atoms" preferably means methyl, ethyl, n-propyl, i-propyl, c-propyl, isopropyl, n-butyl, i-butyl, t-butyl, n-pentyl or n-hexyl radicals.

The term "linear or branched alkyl having from 1 to 15 carbon atoms" especially means methyl, ethyl, propyl, isopropyl, cyclopropyl, n-butyl, i-butyl, t-butyl, n-pentyl, n-hexyl, 2-ethylhexyl, octyl or dodecyl radicals. When the alkyl radical has from 1 to 20 carbon atoms, it also means hexadecyl or octadecyl radicals.

The term "monohydroxyalkyl" means a radical preferably having from 1 to 6 carbon atoms, especially a hydroxymethyl, 2-hydroxyethyl, 2-hydroxypropyl or 3-hydroxypropyl radical.

The term "polyhydroxyalkyl" means a radical preferably having from 3 to 6 carbon atoms and from 2 to 5 hydroxyl groups, such as 2,3-dihydroxypropyl, 2,3,4-trihydroxybutyl or 2,3,4,5-tetrahydroxypentyl radicals or a pentaerythritol residue.

The term "polyether radical" means a radical having from 2 to 6 carbon atoms interrupted with at least two oxygen atoms, such as methoxymethoxy, methoxyethoxy or methoxyethoxymethoxy radicals.

The term "aryl radical" preferably means a phenyl radical optionally substituted with at least one halogen, an alkyl radical having from 1 to 6 carbon atoms, a hydroxyl, a $C_1$-$C_3$ alkoxy radical, a nitro function, a polyether radical or an amino function optionally protected with an acetyl group or optionally substituted with at least one alkyl radical having from 1 to 6 carbon atoms or an alkoxy radical having from 1 to 6 carbon atoms.

The term "aralkyl radical" preferably means a benzyl or phenethyl radical optionally substituted with at least one halogen, an alkyl radical having from 1 to 6 carbon atoms, a hydroxyl, an alkoxy radical having from 1 to 3 carbon atoms, a nitro function, a polyether radical or an amino function optionally protected with an acetyl group or optionally substituted with at least one alkyl radical having from 1 to 6 carbon atoms or an alkoxy radical having from 1 to 6 carbon atoms.

The term "alkenyl radical" means a radical preferably having from 2 to 5 carbon atoms and having one or more ethylenic unsaturations, more particularly such as an allyl radical.

The term "sugar residue" means a residue derived especially from glucose, galactose or mannose, or, alternatively, from glucuronic acid, such as 6'-mannosyl, 6'-glucosyl or 6'-galactosyl.

The term "amino acid residue" especially means a residue derived from lysine, from glycine or from aspartic acid, and the term "peptide residue" more particularly means a dipeptide or tripeptide residue resulting from the combination of amino acids.

According to the present invention, the compounds of formula (I) that are more particularly preferred are those for which at least one and preferably all of the conditions below are satisfied:

R1 is a radical —OR7;
R2 is a hydrogen or an —OH;
R5 and R6, which may be identical or different, are each a methyl radical or an ethyl radical, or together form a pyrrolidine heterocycle;
Q is a radical —OR13.

Among the compounds of formula (I) according to the present invention, especially representative are the following compounds:

1. 4-[2-(3-tert-Butyl-4-diethylaminophenyl)-2-hydroxyiminoethoxy]benzoic acid;
2. 4-[2-(3-tert-Butyl-4-diethylaminophenyl)-2-hydroxyiminoethoxy]-2-hydroxybenzoic acid;
3. 4-[2-(3-tert-Butyl-4-pyrrolidin-1-ylphenyl)-2-hydroxyiminoethoxy]benzoic acid;
4. 4-[2-(3-tert-Butyl-4-pyrrolidin-1-ylphenyl)-2-hydroxyiminoethoxy]-2-hydroxybenzoic acid;
5. 4-{2-[4-(Acetylethylamino)-3-tert-butylphenyl]-2-hydroxyiminoethoxy}benzoic acid;
6. 4-{2-[4-(Acetylethylamino)-3-tert-butylphenyl]-2-hydroxyiminoethoxy}-2-hydroxybenzoic acid;

7. Ethyl 4-[2-(3-tert-butyl4-diethylaminophenyl)-2-hydroxyiminoethoxy]-2-hydroxybenzoate;
8. Isopropyl 4-[2-(3-tert-butyl4-diethylaminophenyl)-2-hydroxyiminoethoxy]2-hydroxybenzoate;
9. Isobutyl 4-[2-(3-tert-butyl4-diethylaminophenyl)-2-hydroxyiminoethoxy]-2-hydroxybenzoate;
10. Octyl 4-[2-(3-tert-butyl4-diethylaminophenyl)-2-hydroxyiminoethoxy]-2-hydroxybenzoate;
11. Dodecyl 4-[2-(3-tert-butyl-4-diethylaminophenyl)-2-hydroxyiminoethoxy]-2-hydroxybenzoate;
12. 1-(3-tert-Butyl-4-diethylaminophenyl)-2-[3-hydroxy-4-(morpholine-4-carbonyl)phenoxy]ethanone oxime;
13. 4-[2-(3-tert-Butyl-4-diethylaminophenyl)-2-hydroxyiminoethoxy]-N-ethyl-2-hydroxy-N-methylbenzamide;
14. 4-[2-(3-tert-Butyl-4-diethylaminophenyl)-2-hydroxyiminoethylsulfanyl]-2-hydroxybenzoic acid;
15. 4-[2-(3-tert-Butyl-4-diethylaminophenyl)-2-hydroxyiminoethylsulfanyl]benzoic acid;
16. 4-[2-(3-tert-Butyl-4-diethylaminophenyl)-2-hydroxyiminoethylamino]-2-hydroxybenzoic acid;
17. 4-{[2-(3-tert-Butyl-4-diethylaminophenyl)-2-hydroxyiminoethyl]methylamino}-2-hydroxybenzoic acid;
18. 4-[3-(3-tert-Butyl-4-diethylaminophenyl)-3-hydroxyiminopropyl]-2-hydroxybenzoic acid;
19. 4-[2-(3-tert-Butyl-4-diethylaminophenyl)-2-hydroxyiminoacetylamino]-2-hydroxybenzoic acid;
20. 4-[2-(3-tert-Butyl-4-diethylaminophenyl)-2-hydroxyiminoacetylamino]benzoic acid;
21. 4-[2-(3-tert-Butyl-4-diethylaminophenyl)-2-methoxyiminoacetylamino]-2-hydroxybenzoic acid;
22. 4-[2-(3-tert-Butyl-4-diethylaminophenyl)-2-methoxyiminoethoxy]-2-hydroxybenzoic acid;
23. 4-[2-(3-tert-Butyl-4-diethylaminophenyl)-2-(methylhydrazono)ethoxy]-2-hydroxybenzoic acid;
24. 4-[2-(3-tert-Butyl-4-diethylaminophenyl)-2-(pentylhydrazono)ethoxy]-2-hydroxybenzoic acid;
25. 4-[2-(3-tert-Butyl-4-diethylaminophenyl)-2-methanesulfonyliminoethoxy]-2-hydroxybenzoic acid;
26. 4-[2-(3-tert-Butyl-4-diethylaminophenyl)-2-(pentane-1-sulfonylimino)ethoxy]-2-hydroxybenzoic acid;
27. 4-[2-(3-tert-Butyl-5-chloro-4-diethylaminophenyl)-2-hydroxyiminoethoxy]-2-hydroxybenzoic acid;
28. 4-[2-(3-tert-Butyl-4-diethylamino-5-fluorophenyl)-2-hydroxyiminoethoxy]-2-hydroxybenzoic acid;
29. 4-[2-(3-tert-Butyl-4-diethylamino-5-trifluoromethylphenyl)-2-hydroxyiminoethoxy]-2-hydroxybenzoic acid;
30. 4-[2-(3-tert-Butyl-4-diethylamino-5-methylphenyl)-2-hydroxyiminoethoxy]-2-hydroxybenzoic acid;
31. 4-[2-(3-tert-Butyl-4-diethylamino-5-ethylphenyl)-2-hydroxyiminoethoxy]-2-hydroxybenzoic acid;
32. 4-{2-[3-tert-Butyl-4-diethylamino-5-(2-ethoxyethoxy)phenyl]-2-hydroxyiminoethoxy}-2-hydroxybenzoic acid;
33. 4-[2-(4-diethylamino-5-propoxyphenyl)-2-hydroxyiminoethoxy]-2-hydroxybenzoic acid;
34. 4-[2-(4-diethylamino-3-isopropylphenyl)-2-hydroxyiminoethoxy]-2-hydroxybenzoic acid;
35. 4-[2-(4-diethylamino-3-trifluoromethylphenyl)-2-hydroxyiminoethoxy]-2-hydroxybenzoic acid;
36. 4-[2-(4-diethylaminophenyl)-2-hydroxyiminoethoxy]-2-hydroxybenzoic acid;
37. 4-{2-[3-tert-Butyl-4-(ethylmethylamino)phenyl]-2-hydroxyiminoethoxy}-2-hydroxybenzoic acid;
38. 4-[2-(3-tert-Butyl-4-dimethylaminophenyl)-2-hydroxyiminoethoxy]-2-hydroxybenzoic acid;
39. 4-{2-[3-tert-Butyl-4-(ethylisobutylamino)phenyl]-2-hydroxyiminoethoxy}-2-hydroxybenzoic acid;
40. 4-[2-(3-tert-Butyl-4-morpholin-4-ylphenyl)-2-hydroxyiminoethoxy]-2-hydroxybenzoic acid;
41. 4-[2-(3-tert-Butyl-4-piperid-1-ylphenyl)-2-hydroxyiminoethoxy]-2-hydroxybenzoic acid;
42. 4-{2-[3-tert-Butyl-4-(2-oxopiperid-1-yl)phenyl]-2-hydroxyiminoethoxy}benzoic acid;
43. 4-{2-[3-tert-Butyl-4-(2-oxopyrrolidin-1-yl)phenyl]-2-hydroxyiminoethoxy}benzoic acid;
44. 4-[2-(3-tert-Butyl-4-ethylaminophenyl)-2-hydroxyiminoethoxy]-2-hydroxybenzoic acid;
45. 4-{2-[4-(Ethylpropionylamino)-3-tert-butylphenyl]-2-hydroxyiminoethoxy}-2-hydroxybenzoic acid;
46. 4-{2-[3-tert-Butyl-4-(ethoxycarbonylethylamino)phenyl]-2-hydroxyiminoethoxy}-2-hydroxybenzoic acid;
47. 4-{2-[3-tert-Butyl-4-(ethylmethoxycarbonylamino)phenyl]-2-hydroxyiminoethoxy}-2-hydroxybenzoic acid;
48. 4-{2-[4-(Ethyltrifluoroacetylamino)-3-tert-butylphenyl]-2-hydroxyiminoethoxy}-2-hydroxybenzoic acid;
49. 4-{2-[4-(Trifluoroacetylamino)-3-tert-butylphenyl]-2-hydroxyiminoethoxy}-2-hydroxybenzoic acid;
50. 4-{2-[3-tert-Butyl-4-(ethylisopropylamino)phenyl]-2-hydroxyiminoethoxy}-2-hydroxybenzoic acid.

The present invention also features processes for preparing the compounds of formula (I), in particular according to the reaction schemes set forth in the FIGURE of Drawing.

The claimed compounds may be obtained from starting materials of type 1. After a step of disubstitution of the aniline function ($R_5=R_6$) or else two steps of substitution of this function, for example by acetylation (AcCl, Et$_3$N) followed by alkylation (for example NaH, Alkyl-I), or alternatively a single step of substitution ($R_5=H$), for example an alkylation (NaH, Alkyl-I), the compounds having the general structure of type 2 are obtained.

A Friedel-Crafts acylation makes it possible to obtain the compounds of structure 3 and 6, respectively, by reaction of acetyl chloride or ethyloxalyl chloride in the presence of a Lewis acid, for instance AlCl$_3$.

An α-halogenation of 3, followed by a nucleophilic substitution with the phenol, thiophenol or aniline chemical function of the partner corresponding to the end product makes it possible to obtain the compounds of structure 4, when Y=O, S, N—$R_{17}$, respectively. To obtain the products for which Y=CH$_2$, the acetyl function of 3 may be reacted with a benzaldehyde function in the presence of base, for instance using 4-carboxybenzaldehyde and NaOH. The chalcone function is then reduced by catalytic hydrogenation.

Finally, the compounds of structure 5 may be obtained by reacting a ketone function with derivatives of the type Q-NH$_2$ in ethanol, for instance hydroxylamine (Q=OH). In the case where $R_1$=OH, a saponification step is then necessary, by reaction of the intermediate ester with aqueous NaOH, for example. The compounds of general structure 7 may be obtained from compounds of type 6 via saponification of the ester function followed by peptide coupling with an aniline derivative, for instance ethyl 4-aminobenzoate. As for the transition 4-5, the compounds of general structure 8 may be obtained by reacting the ketone function with derivatives of the type Q-NH$_2$ in ethanol, for instance hydroxylamine (Q=OH). In the case where $R_1$=OH, a saponification step is then necessary, by reacting the intermediate ester with aqueous NaOH, for example.

The compounds according to the invention have activating properties on RAR-type receptors. This RAR-receptor-activating activity is measured in a test of transactivation by means of the dissociation constant Kdapp (apparent) and the $AC_{50}$ (concentration that gives 50% of the activity of the reference molecule).

According to the present invention, the expression "activator of RAR-type receptors" means any compound which, for at least one of the RAR subtypes, has a dissociation constant Kdapp and an $AC_{50}$ value of less than or equal to 1 µM, in a transactivation test as described in Example 7 to follow.

The preferred compounds of the present invention have, for at least one of the RAR subtypes, a dissociation constant Kdapp of less than or equal to 500 nM and advantageously less than or equal to 100 nM, and an $AC_{50} \leq 100$ nM.

The present invention also features the compounds of formula (I) as described above, as medicinal active agents.

The compounds according to the invention are particularly suitable in the following fields of treatment:

- for treating dermatological complaints, conditions or afflictions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;
- for treating other types of keratinization disorders, especially ichthyosis, ichthyosiform conditions, Darier's disease, palmoplantar keratoderma, leukoplakia and leukoplakiform conditions, and cutaneous or mucous (buccal) lichen;
- for treating other dermatological complaints, conditions or afflictions with an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or alternatively gingival hypertrophy;
- for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basocellular and spinocellular epithelioma, and also any precancerous skin lesion such as keratoacanthomas;
- for treating other dermatological disorders such as immune dermatoses, such as lupus erythematosus, immune bullous diseases and collagen diseases, such as scleroderma;
- in the treatment of dermatological or general complaints, conditions or afflictions with an immunological component;
- for treating certain ophthalmological disorders, especially corneopathies;
- for preventing or curing the stigmata of epidermal and/or dermal atrophy induced by local or systemic corticosteroids, or any other form of cutaneous atrophy;
- in the treatment of any cutaneous or general complaint, condition or affliction of viral origin;
- in the treatment of skin disorders caused by exposure to UV radiation, and also for repairing or combating aging of the skin, whether photoinduced or chronological aging, or for reducing actinic pigmentations and keratosis, or any pathology associated with chronological or actinic aging, such as xerosis;
- for combating sebaceous function disorders, such as the hyperseborrhoea of acne or simple seborrhoea;
- for preventing or treating cicatrization disorders, or for preventing or repairing stretch marks, or alternatively for promoting cicatrization;
- in the treatment of pigmentation disorders, such as hyperpigmentation, melasma, hypopigmentation or vitiligo;
- in the treatment of lipid metabolism complaints, conditions or afflictions such as obesity, hyperlipidaemia, or non-insulin-dependent diabetes;
- in the treatment of inflammatory complaints, conditions or afflictions such as arthritis;
- in the treatment or prevention of cancerous or precancerous conditions;
- in the prevention or treatment of alopecia of various origins, especially alopecia caused by chemotherapy or radiation;
- in the treatment of disorders of the immune system, such as asthma, type I sugar diabetes, multiple sclerosis or other selective dysfunctions of the immune system; and
- in the treatment of complaints, conditions or afflictions of the cardiovascular system, such as arteriosclerosis or hypertension.

The present invention also features pharmaceutical compositions comprising, formulated into a physiologically acceptable medium, at least one compound of formula (I) as defined above.

The present invention also features novel medicinal compositions suited especially for treating the abovementioned complaints, conditions or afflictions which comprise, formulated into a pharmaceutically acceptable support that is compatible with the mode of administration selected for this composition, at least one compound of formula (I), an optical isomer thereof or a salt thereof.

The compositions according to the invention may be administered (regime or regimen) orally, enterally, parenterally, topically or ocularly. The pharmaceutical composition is preferably packaged in a form that is suitable for topical application.

Via the oral route, the composition may be in the form of tablets, gel capsules, dragees, syrups, suspensions, solutions, powders, granules, emulsions, suspensions of microspheres or nanospheres or lipid or polymer vesicles allowing a controlled release. Via the parenteral route, the composition may be in the form of solutions or suspensions for infusion or for injection.

The compounds according to the invention are generally administered at a daily dose of about 0.01 mg/kg to 100 mg/kg of body weight, in 1 to 3 dosages.

The compounds are administered systemically, at a concentration generally of from 0.001% to 10% by weight and preferably from 0.01% to 1% by weight, relative to the total weight of the composition.

Via the topical route, the pharmaceutical compositions according to the invention are more particularly suited for treating the skin and mucous membranes and may be in liquid, pasty or solid form, and more particularly in the form of ointments, creams, milks, pomades, powders, impregnated pads, syndets, solutions, gels, sprays, mousses, suspensions, sticks, shampoos or washing bases. They may also be in the form of suspensions of microspheres or nanospheres or of lipid or polymer vesicles or gelled or polymer patches allowing a controlled release.

The compounds are administered topically at a concentration generally of from 0.001% to 10% by weight and preferably from 0.01% to 1% by weight, relative to the total weight of the composition.

The compounds of formula (I) according to the invention also find an application in cosmetics, in particular in body and hair hygiene and especially for treating acne-prone skin, for promoting regrowth of the hair or for limiting hair loss, for combating the greasy appearance of the skin or the hair, in protection against the harmful aspects of sunlight or in the treatment of physiologically dry skin, and for preventing and/or combating photoinduced or chronological aging.

This invention thus also features cosmetic compositions comprising, formulated into a physiologically acceptable support, at least one of the compounds of formula (I).

This invention also features the non-therapeutic administration of a cosmetic composition comprising at least one compound of formula (I) for preventing and/or treating the signs of aging and/or dry skin.

The present invention also features the non-therapeutic administration of a cosmetic composition comprising at least one compound of formula (I) for body or hair hygiene.

The cosmetic compositions according to the invention containing, in a physiologically acceptable support, at least one compound of formula (I) or an optical or geometrical isomer thereof or a salt thereof, may be especially in the form of a cream, a milk, a gel, suspensions of microspheres or nanospheres or lipid or polymer vesicles, impregnated pads, solutions, sprays, mousses, sticks, soaps, washing bases or shampoos.

The concentration of compound of formula (I) in the cosmetic composition is preferably from 0.001% to 3% by weight, relative to the total weight of the composition.

The term "physiologically acceptable medium" means a medium that is compatible with the skin and optionally with its integuments (eyelashes, nails or hair) and/or mucous membranes.

The pharmaceutical and cosmetic compositions as described above may also contain inert additives, or even pharmacodynamically active additives as regards the pharmaceutical compositions, or combinations of these additives, and especially:

wetting agents;
flavor enhancers;
preservatives such as para-hydroxybenzoic acid esters;
stabilizers;
moisture regulators;
pH regulators;
osmotic pressure modifiers;
emulsifiers;
UV-A and UV-B screening agents;
antioxidants such as α-tocopherol, butylhydroxyanisole, butylhydroxytoluene, superoxide dismutase, ubiquinol or certain metal-chelating agents;
depigmenting agents such as hydroquinone, azelaic acid, caffeic acid or kojic acid;
emollients;
moisturizers, for example glycerol, PEG 400, thiamorpholinone and its derivatives or urea;
anti-seborrhoeic or anti-acne agents, such as S-carboxymethylcysteine, S-benzylcysteamine, salts thereof or derivatives thereof, or benzoyl peroxide;
antibiotics, for example erythromycin and its esters, neomycin, clindamycin and its esters, and tetracyclines;
anti-fungal agents such as ketoconazole or poly-4,5-methylene-3-isothiazolidones;
agents for promoting regrowth of the hair, for instance Minoxidil (2,4-diamino-6-piperidinopyrimidine 3-oxide) and its derivatives, Diazoxide (7-chloro-3-methyl-1,2,4-benzothiadiazine 1,1-dioxide) and Phenytoin (5,4-diphenylimidazolidine-2,4-dione);
non-steroidal anti-inflammatory agents;
carotenoids and especially β-carotene;
anti-psoriatic agents such as anthralin and its derivatives;
eicosa-5,8,11,14-tetraynoic acid and eicosa-5,8,11-triynoic acid, and esters and amides thereof;
retinoids, i.e., natural or synthetic RXR receptor ligands;
corticosteroids or oestrogens;
α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and its salts, amides or esters;
ion-channel blockers such as potassium-channel blockers;
or alternatively, more particularly for pharmaceutical compositions, in combination with medicinal active agents known to interfere with the immune system (for example cyclosporin, FK 506, glucocorticoids, monoclonal antibodies, cytokines or growth factors, etc.).

Of course, one skilled in this art will take care to select the optional compound(s) to be added to these compositions such that the advantageous properties intrinsically attached to the present invention are not, or are not substantially, adversely affected by the envisaged addition.

The present invention also features a cosmetic regime or regimen for enhancing the appearance of the skin, wherein a composition comprising at least one compound of formula (I) as defined above is applied to the skin.

Activation of the retinoic acid receptors with the compounds of formula (I) according to the invention makes it possible to obtain skin of enhanced surface appearance.

Several examples of the production of bioactive compounds of formula (I) according to the invention, biological activity results and also various specific formulations based on such compounds, will now be given, it being understood that same are intended only as illustrative and in nowise limitative. In said examples to follow, all parts and percentages are given by weight, unless otherwise indicated.

EXAMPLES:

Example 1

Synthesis of 4-[2-(3-tert-Butyl-4-diethylaminophenyl)-2-hydroxyiminoethoxy]benzoic acid:

a. Preparation of 4-Bromo-2-tert-butylaniline:

51.8 g (347 mmol) of 2-tert-butylaniline (commercial product marketed especially by the company Aldrich) are dissolved in 600 ml of glacial acetic acid. 900 ml of aqueous 48% hydrobromic acid are then added, and the reaction medium is then cooled to 0° C. 300 ml of DMSO are then added dropwise, after which the reaction medium is warmed to room temperature. After stirring for 4 hours, 250 ml of ethyl acetate are added, followed by 400 ml of 5N sodium hydroxide, and then 1.75 l of 10N sodium hydroxide, to bring the pH to 8. 250 ml of ethyl acetate are added and the medium is separated by settling of the phases. The aqueous phase is then re-extracted with 500 ml of ethyl acetate. The combined organic phases are then rinsed with 1 l of water, and then concentrated under reduced pressure. The residue obtained is purified by chromatography (eluent: 95/5 heptane/ethyl acetate). An orange-colored oil is obtained (m=56.2 g, yield=71%).

b. Preparation of (4-Bromo-2-tert-butylphenyl)diethylamine:

20 g (88 mmol) of 4-bromo-2-tert-butylaniline are dissolved in 200 ml of DMSO under a nitrogen atmosphere. 7.7 g (190 mmol) of sodium hydride are added portionwise. After stirring for 30 minutes, 15.4 ml (190 mmol) of ethyl iodide are added dropwise. The reaction medium is stirred for 12 hours and then poured into saturated ammonium chloride solution. After extraction with ethyl acetate, the reaction sequence is repeated, and the residue is then purified by chromatography on a column of silica (eluent: 98/2 heptane/ethyl acetate). A colorless oil is obtained (m=16.7 g, yield=67%).

c. Preparation of 3-tert-Butyl-4-diethylaminobenzaldehyde:

16.7 g (58 mmol) of (4-bromo-2-tert-butyl phenyl)diethylamine are dissolved in 250 ml of anhydrous THF and the mixture is cooled to −78° C. 35 ml (88 mmol) of 2.5 M butyllithium solution are added dropwise and the medium is then stirred for 30 minutes. 6.9 ml (88 mmol) of dimethylformamide are added dropwise and the reaction medium is then warmed slowly to room temperature. After stirring for one hour, the reaction medium is treated with saturated ammonium chloride solution and extracted with ethyl acetate. The residue obtained is purified by chromatography on a column of silica. A yellow oil is obtained (m=11.5 g, yield=85%).

d. Preparation of 3-tert-Butyl-4-diethylaminoacetophenone:

11.5 g (49 mmol) of 3-tert-butyl-4-diethylaminobenzaldehyde are dissolved in 200 ml of THF. 3 M methylmagnesium bromide solution (21 ml, 63 mmol) is added and the medium is then stirred for 2 hours. After treatment with saturated ammonium chloride solution followed by extraction with ethyl acetate, the crude residue obtained is dissolved in 200 ml of dichloromethane and 10 g (120 mmol) of manganese dioxide are added. The reaction medium is stirred for 24 hours, and a further 10 g of $MnO_2$ are then added. After stirring for 12 hours, the reaction medium is filtered and the filtrate is concentrated under reduced pressure. The residue obtained is purified by chromatography on a column of silica (eluent: 9/10 heptane/ethyl acetate). A yellow oil is obtained (m=5.6 g, yield=46%).

e. Preparation of 2-Bromo-1-(3-tert-butyl-4-diethylaminophenyl)ethanone:

2.1 g (8 mmol) of 3-tert-butyl-4-diethylaminoacetophenone are dissolved in 250 ml of ethyl ether and 25 ml of dioxane. A solution of dibromine (0.43 ml in 50 ml of dichloromethane, 8 mmol) is added dropwise over 1 hour 30 minutes at 0° C. The solution obtained is then poured into ice-cold water and the organic phase is washed with saturated sodium thiosulfate solution. The residue obtained after concentration is purified by chromatography (eluent: 99/1 heptane/ethyl acetate). A yellow oil is obtained (m=2 g, yield=73%).

f. Preparation of Methyl 4-[2-(3-tert-butyl-4-diethylaminophenyl)-2-oxoethoxy]benzoate:

1 g (3 mmdl) of 2-bromo-1-(3-tert-butyl-4-diethylaminophenyl)ethanone and 444 mg (3 mmol) of methyl 4-hydroxybenzoate are dissolved in 50 ml of 2-butanone. 440 mg (3 mmol) of potassium carbonate and a catalytic amount of 18-crown-6 are added. The reaction medium is refluxed for 12 hours and then filtered and concentrated under reduced pressure. The residue obtained is purified by chromatography (eluent: 9/1 heptane/ethyl acetate). A white solid is obtained (m.p.=92° C., m=620 mg, yield=54%).

g. Preparation of Methyl 4-[2-(3-tert-butyl-4-diethylaminophenyl)-2-hydroxyiminoethoxy]benzoate:

620 mg (1.6 mmol) of methyl 4-[2-(3-tert-butyl-4-diethylaminophenyl)-2-oxoethoxy]benzoate are dissolved in 30 ml of THF and 30 ml of methanol. 0.63 ml (7.8 mmol) of pyridine and 540 mg (7.8 mmol) of hydroxylamine hydrochloride are added. The reaction medium is refluxed for 1 hour 30 minutes and then, after cooling, is poured into saturated ammonium chloride solution. After extraction with ethyl acetate and concentration, the residue is purified by chromatography (eluent 9/1 heptane/ethyl acetate). The two isomers are isolated separately: the syn-isomer is the major product (m=550 mg, yield=83%) and the anti-isomer is the minor product (m=90 mg, yield=13%).

h. Synthesis of 4-[2-(3-tert-Butyl-4-diethylaminophenyl)-2-hydroxyiminoethoxy]benzoic acid:

550 mg (1.4 mmol) of methyl 4-[2-(3-tert-butyl-4-diethylaminophenyl)-2-hydroxyiminoethoxy]benzoate are dissolved in 10 ml of THF. 1 ml of methanol is added, followed by addition of 164 mg (4 mmol) of powdered sodium hydroxide and 100 μl water. The reaction medium is stirred at room temperature for 12 hours and then treated with saturated ammonium chloride solution. The aqueous phase is returned to pH 5 by adding 1N hydrochloric acid, and is extracted twice with ethyl acetate. The residue obtained is purified by chromatography on a column of silica (eluent: 80/20 and then 50/50 heptane/heptane). The final product is then recrystallized from a heptane/acetone system. A white crystalline solid is obtained (m.p.=185° C., m=245 mg, yield=44%); ($^1$H NMR ($CDCl_3$): 1.04-1.07 (t, 6H); 1.45 (s, 9H); 2.89 (m, 4H); 5.36 (s, 2H); 7.00-7.02 (d, J=8.8 Hz, 2H); 7.22-7.25 (d, J=8.3 Hz, 1H); 7.44-7.46 (dd, J=6.2 Hz, J'=2.06 Hz, 1H); 7.72 (d, J=2.0 Hz, 1H); 8.03-8.05 (d, J=8.74 Hz, 2H)).

Example 2

Synthesis of 4-[2-(3-tert-Butyl-4-diethylaminophenyl)-2-hydroxyiminoethoxy]-2-hydroxybenzoic acid:

a. Preparation of Methyl 4-[2-(3-tert-butyl-4-diethylaminophenyl)-2-oxoethoxy]-2-hydroxybenzoate:

In a manner similar to that of Example 1.f, by reaction of 800 mg (2.5 mmol) of 2-bromo-1-(3-tert-butyl-4-diethylaminophenyl)ethanone (Example 1.e) and 386 mg (2.3 mmol) of methyl 2,4-dihydroxybenzoate in the presence of 350 mg (2.5 mmol) of potassium carbonate and a catalytic amount of 18-crown-6. A brown oil is obtained (m=600 mg, yield=63%).

b. Preparation of Methyl 4-[2-(3-tert-butyl4-diethylaminophenyl)-2-hydroxyiminoethoxy]-2-hydroxybenzoate:

In a manner similar to that of Example 1.g, by reaction of 300 mg (0.7 mmol) of methyl 4-[2-(3-tert-butyl-4-diethylaminophenyl)-2-oxoethoxy]-2-hydroxybenzoate in the presence of 0.3 ml (3.6 mmol) of pyridine and 250 mg (3.6 mmol) of hydroxylamine hydrochloride. The two isomers are isolated separately: the syn-isomer is the major product (m=120 mg, yield=39%) and the anti-isomer is the minor product (m=50 mg, yield=16%).

c. Synthesis of 4-[2-(3-tert-Butyl-4-diethylaminophenyl)-2-hydroxyiminoethoxy]-2-hydroxybenzoic acid:

In a manner similar to that of Example 1.g, by reaction of 120 mg (0.3 mmol) of methyl 4-[2-(3-tert-butyl-4-diethylaminophenyl)-2-hydroxyiminoethoxy]-2-hydroxybenzoate with 46 mg (1.4 mmol) of powdered sodium hydroxide. The final product is then recrystallized from a heptane/ethyl ether system. A white crystalline solid is obtained (m.p.=210° C., m=60 mg, yield=48%); ($^1$H NMR (DMSO): 0.96-1.00 (t, 6H); 1.38 (s, 9H); 2.7-3 (m, 4H); 5.26 (s, 2H); 6.46-6.49 (dd, J=6.4 Hz, J'=2.4 Hz, 1H); 6.55 (d, J=2.4 Hz, 1H); 7.26-7.28

(d, J=8.3 Hz, 1H); 7.46-7.48 (dd, J=6.2 Hz, J'=2.03 Hz,1H); 7.65-7.67 (d, J=8.8 Hz, 1H); 7.69 (d, J=2.03 Hz, 1H); 11.9 (s, 1H); 13-14 (s, 1H)).

Example 3

Synthesis of 4-[2-(3-tert-Butyl-4-pyrrolidin-1-ylphenyl)-2-hydroxyiminoethoxy]benzoic acid:

a. Preparation of 1-(4-Bromo-2-tert-butylphenyl)pyrrolidine:

In a manner similar to that of Example 1.b, by reaction of 20 g (88 mmol) of 4-bromo-2-tert-butylaniline with 7.6 g (194 mmol) of sodium hydride and 22.2 ml (194 mmol) of dibromobutane. A yellow oil is obtained (m=18 g, yield=73%).

b. Preparation of 3-tert-Butyl-4-pyrrolidin-1-ylbenzaldehyde:

In a manner similar to that of Example 1.c, by reaction of 10 g (35 mmol) of 1-(4-bromo-2-tert-butylphenyl)pyrrolidine with 21 ml of 2.5 M butyllithium and 4 ml (53 mmol) of dimethylformamide. A yellow oil is obtained (m=4.3 g, yield=53%).

c. Preparation of 3-tert-Butyl-4-pyrrolidin-1-ylacetophenone:

In a manner similar to that of Example 1.d, by reaction of 4.3 g (19 mmol) of 3-tert-butyl-4-pyrrolidin-1-ylbenzaldehyde with 8.2 ml of 3M methylmagnesium bromide solution and then with 15.3 g (180 mmol) of manganese dioxide. An orange-colored oil is obtained (m=2.3 g, yield=52%).

d. Preparation of 2-Bromo-1-(3-tert-butyl-4-pyrrolidin-1-ylphenyl)ethanone:

In a manner similar to that of Example 1.e, by reaction of 2.3 g (9.4 mmol) of 3-tert-butyl-4-pyrrolidin-1-ylacetophenone with 240 µl of dibromine. A yellow oil is obtained (m=2.3 g, yield=76%).

Preparation of Methyl 4-[2-(3-tert-butyl-4-pyrrolidin-1-ylphenyl)-2-oxoethoxy]benzoate:

In a manner similar to that of Example 1.f, by reaction of 600 mg (1.9 mmol) of 2-bromo-1-(3-tert-butyl-4-pyrrolidin-1-ylphenyl)ethanone and 268 mg (1.8 mmol) of methyl 4-hydroxybenzoate, followed by 248 mg (2 mmol) of potassium carbonate and a catalytic amount of 18-crown-6. An orange-colored oil is obtained (m=400 mg, yield=53%).

f. Preparation of Methyl 4-[2-(3-tert-butyl-4-pyrrolidin-1-ylphenyl)-2-hydroxyiminoethoxy]benzoate:

In a manner similar to that of Example 1.g, by reaction of 400 mg (1 mmol) of methyl 4-[2-(3-tert-butyl-4-pyrrolidin-1-ylphenyl)-2-oxoethoxy]benzoate with 0.4 ml (5 mmol) of pyridine and 352 mg (5 mmol) of hydroxylamine hydrochloride. A pinkish solid is obtained (m.p.=170° C., m=210 mg, yield=51%).

g. Synthesis of 4-[2-(3-tert-Butyl-4-pyrrolidin-1-ylphenyl)-2-hydroxyiminoethoxy]benzoic acid:

In a manner similar to that of Example 1.h, by reaction of 210 mg (0.5 mmol) of methyl 4-[2-(3-tert-butyl-4-pyrrolidin-1-ylphenyl)-2-hydroxyiminoethoxy]benzoate with 100 mg (2.5 mmol) of sodium hydroxide. A white solid is obtained after recrystallization (m.p.=235° C., m=44 mg, yield=22%); ($^1$H NMR (DMSO): 1.35 (s, 9H); 1.86 (s, 4H); 2.89 (s, 4H); 5.29 (s, 2H); 7.04-7.06 (d, J=7.65 Hz, 2H); 7.40-7.42 (d, J=7.4 Hz, 1H); 7.49-7.51 (d, J=7.4 Hz, 1H); 7.65 (s, 1H); 7.86-7.88 (d, J=7.4 Hz, 2H); 11.9 (s, 1H); 12.6 (s, 1H)).

Example 4

Synthesis of 4-[2-(3-tert-Butyl-4-pyrrolidin-1-ylphenyl)-2-hydroxyiminoethoxy]-2-hydroxybenzoic acid:

a. Preparation of Methyl 4-[2-(3-tert-butyl-4-pyrrolidin-1-ylphenyl)-2-oxoethoxy]-2-hydroxybenzoate:

In a manner similar to that of Example 1.f, by reaction of 600 mg (1.9 mmol) of 2-bromo-1-(3-tert-butyl-4-pyrrolidin-1-ylphenyl)ethanone (Example 1.e) and 302 mg (1.8 mmol) of methyl 2,4-dihydroxybenzoate in the presence of 250 mg (2 mmol) of potassium carbonate and a catalytic amount of 18-crown-6. A brown oil is obtained (m=350 mg, yield=47%).

b. Preparation of Methyl 4-[2-(3-tert-butyl-4-pyrrolidin-1-ylphenyl)-2-hydroxyiminoethoxy]-2-hydroxybenzoate:

In a manner similar to that of Example 1.g, by reaction of 350 mg (0.85 mmol) of methyl 4-[2-(3-tert-butyl4-pyrrolidin-1-ylphenyl)-2-oxoethoxy]-2-hydroxybenzoate in the presence of 0.35 ml (4.3 mmol) of pyridine and 300 mg (4.3 mmol) of hydroxylamine hydrochloride. The two isomers are isolated separately: the syn-isomer is the major product, in the form of a pinkish solid (m.p.=149° C., m=193 mg, yield=53%).

c. Synthesis of 4-[2-(3-tert-Butyl-4-pyrrolidin-1-ylphenyl)-2-hydroxyiminoethoxy]-2-hydroxybenzoic acid:

In a manner similar to that of Example 1.g, by reaction of 193 mg (0.45 mmol) of methyl 4-[2-(3-tert-butyl4-pyrrolidin-1-ylphenyl)-2-hydroxyiminoethoxy]-2-hydroxybenzoate with 90 mg (2.3 mmol) of powdered sodium hydroxide. The final product is then recrystallized from a heptane/ethyl ether system. A beige-colored crystalline solid is obtained (m.p.=234° C., m=25 mg, yield=13%); ($^1$H NMR (DMSO): 1.35 (s, 9H); 1.86 (s, 4H); 2.89 (s, 4H); 5.26 (s, 2H); 6.46-6.49 (d, J=8.6 Hz, 1H); 6.5 (s, 1 H); 7.40-7.42 (d, J=8.2 Hz, 1H); 7.49-7.51 (d, J=7.9 Hz, 1H); 7.66-7.68 (d, J=8.5 Hz, 2H); 11.9 (s, 1H)).

Example 5

Synthesis of 4-{2-[4-(Acetylethylamino)-3-tert-butyl-phenyl]-2-hydroxyiminoethoxy}benzoic acid:

a. Preparation of N-(2-tert-Butylphenyl)acetamide:

40 g (268 mmol) of 2-tert-butylaniline (commercial product marketed especially by the company Aldrich) are dissolved in 700 ml of THF. 32.5 g (320 mmol) of triethylamine are added and the medium is cooled to 5° C. 21 ml (295 mmol) of acetyl chloride are added and the reaction is stirred for 2 hours and then poured into water. After extraction with ethyl acetate and rinsing with water, followed by concentration, a cottony solid is obtained (m.p.=163° C., m=49.4 g, yield=97%).

b. Preparation of N-(4-Bromo-2-tert-butylphenyl)acetamide:

45 g (235 mmol) of N-(2-tert-butylphenyl)acetamide are dissolved in 450 ml of dichloromethane. 27.7 g (235 mmol) of N-bromosuccinimide are then added, and the reaction medium is stirred for 48 hours and then filtered. The residue obtained after concentration of the filtrate is dissolved in an ethyl acetate/water mixture and the organic phase is washed with water. The residue obtained is again placed in reaction in the presence of 15 g of N-bromosuccinimide, and then worked up in the same manner after 48 hours. The residue finally obtained is taken up in ethyl acetate, rinsed with sodium thiosulfate solution and then with water, and concentrated under reduced pressure. A pale orange solid is obtained (m=63 g, yield=100%).

c. Preparation of N-(4-Bromo-2-tert-butylphenyl)-N-ethylacetamide:

N-(4-bromo-2-tert-butylphenyl)acetamide are dissolved in 30 ml of DMSO. 420 mg (10.5 mmol) of sodium hydride are added portion wise and the medium is stirred for 20 minutes at room temperature. 1.13 ml (11 mmol) of ethyl iodide are then added and the reaction medium is stirred for 14 hours. After treatment with ammonium chloride solution and extraction with ethyl acetate, the residue obtained is purified by chromatography (eluent: 9/1 and then 75/25 heptane/ethyl acetate). A thick orange oil is obtained (m=2.45 g, yield=82%).

d. Preparation of N-(4-Acetyl-2-tert-butylphenyl)-N-ethylacetamide:

2 g (6.07 mmol) of N-(4-bromo-2-tert-butylphenyl)-N-ethylacetamide, 1.34 g (13.4 mmol) of butyl vinyl ether, 3.73 ml (26.8 mmol) of triethylamine, 60 mg (0.27 mmol) of palladium acetate and 122 mg (0.4 mmol) of tri-o-tolylphosphine are dissolved in 20 ml of acetonitrile. The reaction medium is refluxed for 6 hours and then left at room temperature for 12 hours. After treatment with 1N hydrochloric acid solution and extraction with ethyl acetate, the residue obtained is purified by chromatography (eluent: 90/1 heptane/ethyl acetate). An orange oil is obtained (m=620 mg, yield=35%).

e. Preparation of N-[4-(2-Bromoacetyl)-2-tert-butylphenyl]-N-ethylacetamide:

600 mg (2.3 mmol) of N-(4-acetyl-2-tert-butylphenyl)-N-ethylacetamide are dissolved in 20 ml of THF and the reaction medium is cooled to 0° C. 860 mg (2.3 mmol) of phenyltrimethylammonium tribromide are added and the reaction medium is stirred at room temperature for 14 hours. After treatment with 1N hydrochloric acid solution and extraction with ethyl acetate, the residue obtained is purified by chromatography. A yellow oil is obtained (m=600 mg, yield=77%).

f. Preparation of Allyl 4-{2-[4-(acetylethylamino)-3-tert-butylphenyl]-2-oxoethoxy}benzoate:

In a manner similar to that of Example 1.f, by reaction of 300 mg (0.9 mmol) of N-[4-(2-bromoacetyl)-2-tert-butylphenyl]-N-ethylacetamide with 157 mg (0.9 mmol) of allyl 4-hydroxybenzoate and 134 mg (0.97 mmol) of potassium carbonate. An orange oil is obtained (m=360 mg, yield=94%).

g. Preparation of Allyl 4-{2-[4-(acetylethylamino)-3-tert-butylphenyl]-2-hydroxyiminoethoxy}benzoate:

In a manner similar to that of Example 1.g, by reaction of 360 mg (0.8 mmol) of allyl 4-{2-[4-(acetylethylamino)-3-tert-butylphenyl]-2-oxoethoxy}benzoate with 284 mg (4 mmol) of hydroxylamine hydrochloride and 320 µl of pyridine. A yellowish paste is obtained (m=360 mg, yield=96%).

h. Synthesis of 4-{2-[4-(Acetylethylamino)-3-tert-butylphenyl]-2-oxoethoxy}benzoic acid:

360 mg (0.8 mmol) of allyl 4-{2-[4-(acetylethylamino)-3-tert-butylphenyl]-2-hydroxyiminoethoxy}benzoate are dissolved in 10 ml of THF. 48 mg (0.04 mmol) of tetrakis (triphenylphosphine)palladium are added and the medium is stirred for 5 min. 73 µl (0.8 mmol) of morpholine are then added and the reaction medium is stirred for 15 hours. After treatment with 1N hydrochloric acid solution and extraction with ethyl acetate, the residue is purified by chromatography (eluent: 5/5 heptane/ethyl acetate). A white powder is obtained (m.p.=192° C., m=200 mg, yield=60%); ($^1$H NMR (DMSO): 1.05-1.07 (t, 3H); 1.29 (s, 9H); 1.64 (s, 3H); 2.73 (m, 1H); 4.13 (m, 1H); 5.33 (s, 2H); 6.46 (1H); 6.6 (1H); 7.07-7.09 (d, J=8.1 Hz, 1H); 7.51-7.53 (d, J=8 Hz, 1H); 7.54-7.64 (m, 2H); 7.86 (s, 1H); 12.1 (s, 1H)).

Example 6

Synthesis of 4-{2-[4-(Acetylethylamino)-3-tert-butylphenyl]-2-hydroxyiminoethoxy}-2-hydroxybenzoic acid:

a. Preparation of Allyl 4-{2-[4-(acetylethylamino)-3-tert-butylphenyl]-2-oxoethoxy}-2-hydroxybenzoate:

In a manner similar to that of Example 1.f, by reaction of 300 mg (0.9 mmol) of N-[4-(2-bromoacetyl)-2-tert-butylphenyl]-N-ethylacetamide with 157 mg (0.9 mmol) of allyl 2,4-dihydroxybenzoate and 134 mg (0.97 mmol) of potassium carbonate. An orange oil is obtained (m=370 mg, yield=93%).

b. Preparation of Allyl 4-{2-[4-(acetylethylamino)-3-tert-butylphenyl]-2-hydroxyiminoethoxy}-2-hydroxybenzoate:

In a manner similar to that of Example 1.g, by reaction of 370 mg (0.8 mmol) of allyl 4-{2-[4-(acetylethylamino)-3-tert-butylphenyl]-2-oxoethoxy}-2-hydroxybenzoate with 284 mg (4 mmol) of hydroxylamine hydrochloride and 320 µl of pyridine. A yellowish paste is obtained (m=380 mg, yield=99%).

Synthesis of 4-{2-[4-(Acetylethylamino)-3-tert-butylphenyl]-2-oxoethoxy}-2-hydroxybenzoic acid:

In a manner similar to that of Example 5.h, by reaction of 380 mg (0.8 mmol) of allyl 4-{2-[4-(acetylethylamino)-3-tert-butylphenyl]-2-hydroxyiminoethoxy}-2-hydroxybenzoate with 48 mg (0.04 mmol) of tetrakis(triphenylphosphine)palladium and 73 µl (0.8 mmol) of morpholine. A white powder is obtained (m.p.=199° C., m=200 mg, yield=59%); ($^1$H NMR (DMSO): 1.05-1.08 (t, 3H); 1.29 (s, 9H); 1.64 (s, 3H); 2.7-2.8 (m, 1H); 4.1-4.2 (m, 1H); 5.34 (s, 2H); 6.44-6.47 (dd, J=6.8 Hz, J'=2.2 Hz, 1H); 6.53 (d, J=2 Hz, 1H); 7.07-7.09 (d, J=8.2 Hz, 1H); 7.51-7.53 (dd, J=6 Hz, J'=1.86Hz, 1H); 7.65-7.67 (d, J=8.8 Hz, 1H); 7.86 (d, J=1.78Hz, 1H); 12.2 (s, 1H)).

Example 7

Transactivation Test

The activation of receptors with an agonist (activator) in HeLa cells leads to the expression of a reporter gene, luciferase, which, in the presence of a substrate, generates light. The activation of the receptors may thus be measured by quantifying the luminescence produced after incubating the cells in the presence of a reference antagonist. The activating products displace the antagonist from its site, thus permitting activation of the receptor. The activity is measured by quantifying the increase in light produced. This measurement makes it possible to determine the activating activity of the compounds according to the invention.

In this study, a constant is determined which is the affinity of the molecule for the receptor. Since this value can fluctuate depending on the basal activity and the expression of the receptor, it is referred to as the Kd apparent (KdApp).

To determine this constant, "crossed curves" of the test product against a reference antagonist, 4-(5,5-dimethyl-8-p-tolyl-5,6-dihydro-2-naphthalen-2-ylethynyl)benzoic acid, are performed in 96-well plates. The test product is used at 10 concentrations and the reference antagonist at 7 concentrations. In each well, the cells are in contact with a concentration of the test product and a concentration of the reference antagonist, 4-(5,5-dimethyl-8-p-tolyl-5,6-dihydro-2-naphthalen-2-ylethynyl)benzoic acid. Measurements are also taken for the total agonist (4-[2-(5,5,8,8-tetramethyl-5,6,7,8-tetrahydro-2-naphthyl)propenyl]benzoic acid) and inverse agonist, 4-{(E)-3-[4-(4-tert-butylphenyl)-5,5,8,8-tetramethyl-5,6,7,8-tetrahydro-2-naphthyl]-3-oxopropenyl}benzoic acid, controls.

These crossed curves make it possible to determine the $AC_{50}$ values (concentration at which 50% activation is observed) for the reference ligand at various concentrations of test product. These $AC_{50}$ values are used to calculate the Schild regression by plotting a straight line corresponding to the Schild equation ("Quantitation in Receptor Pharmacology" Terry P. Kenakin, *Receptors and Channels,* 2001, 7, 371-385).

In the case of an agonist, an $AC_{50}$ value (concentration that gives 50% of the activity) is calculated by plotting the curve of the product at the concentration of the reference ligand that gives 80% activation.

The HeLa cell lines used are stable transfectants containing the plasmids ERE-μGlob-Luc-SV-Neo (reporter gene) and RAR (α, β, γ) ER-DBD-puro. These cells are inoculated into 96-well plates at a rate of 10 000 cells per well in 100 μl of DMEM medium without phenol red, and supplemented with 10% defatted calf serum. The plates are then incubated at 37° C. and 7% $CO_2$ for 4 hours.

The various dilutions of the test products, of the reference ligand (4-(5,5-dimethyl-8-p-tolyl-5,6-dihydro-2-naphthalen-2-ylethynyl)benzoic acid), of the 100% control (100 nM 4-[2-(5,5,8,8-tetramethyl-5,6,7,8-tetrahydro-2-naphthyl)propenyl]benzoic acid) and of the 0% control (500 nM 4-{(E)-3-[4-(4-tert-butylphenyl)-5,5,8,8-tetramethyl-5,6,7,8-tetrahydro-2-naphthyl]-3-oxopropenyl}benzoic acid) are added at a rate of 5 μl per well. The plates are then incubated for 18 hours at 37° C. and 7% $CO_2$.

The culture medium is removed by turning over and 100 μl of a 1:1 PBS/luciferin mixture is added to each well. After 5 minutes, the plates are read using the luminescence reader.

| | RAR alpha | | RAR beta | | RAR gamma | |
|---|---|---|---|---|---|---|
| | Kd app (nM) | $AC_{50}$ (nM) | Kd app (nM) | $AC_{50}$ (nM) | Kd app (nM) | $AC_{50}$ (nM) |
| Ex 1 | NA | NA | 500 | 2500 | 60 | 80 |
| Ex 2 | 5000 | 5000 | 500 | 1000 | 4 | 4 |

The results obtained with the compounds according to the invention clearly show Kd app values ≦100 nM and an $AC_{50}$ value ≦100 nM for at least one of the receptor subtypes, this clearly demonstrating an increase in the signal, and in the luminescence in the presence of the reference antagonist. The compounds according to the invention are thus clearly activators of retinoic acid receptors (RAR).

Example 8

Formulation Examples

This example illustrates various specific formulations based on the compounds according to the invention.

A - ORAL ROUTE:

(a) 0.2 g tablet:

| | |
|---|---|
| Compound of Example 6 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampoules:

| | |
|---|---|
| Compound of Example 3 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g tablet:

| | |
|---|---|
| Compound of Example 4 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampoules:

| | |
|---|---|
| Compound of Example 2 | 0.200 g |
| Glycerol | 1.000 g |
| 70% sorbitol | 1.000 g |
| Sodium saccharinate | 0.010 g |
| Methyl para-hydroxybenzoate | 0.080 g |
| Flavoring | qs |
| Purified water | qs 10 ml |

B - PARENTERAL ROUTE:

(a) Composition:

| | |
|---|---|
| Compound of Example 3 | 0.002 g |
| Ethyl oleate | qs 10 g |

(b) Composition:

| | |
|---|---|
| Compound of Example 1 | 0.05% |
| Polyethylene glycol | 20% |
| 0.9% NaCl solution | qs 100 |

(c) Composition:

| | |
|---|---|
| Compound of Example 3 | 2.5% |
| Polyethylene glycol 400 | 20% |
| 0.9% NaCl solution | qs 100 |

(d) Injectable cyclodextrin composition:

| | |
|---|---|
| Compound of Example 3 | 0.1 mg |
| β-Cyclodextrin | 0.10 g |
| Water for injection | qs 10.00 g |

C - TOPICAL ROUTE:

(a) Ointment:

| | |
|---|---|
| Compound of Example 2 | 0.020 g |
| Isopropyl myristate | 81.700 g |
| Liquid petroleum jelly oil | 9.100 g |
| Silica ("Aerosil 200" marketed by Degussa) | 9.180 g |

(b) Ointment:

| | |
|---|---|
| Compound of Example 5 | 0.300 g |
| White petroleum jelly codex | qs 100 g |

(c) Nonionic water-in-oil cream:

| | |
|---|---|
| Compound of Example 4 | 0.100 g |
| Mixture of emulsifying lanolin alcohols, waxes and oils ("Anhydrous Eucerin" marketed by BDF) | 39.900 g |
| Methyl para-hydroxybenzoate | 0.075 g |
| Propyl para-hydroxybenzoate | 0.075 g |
| Sterile demineralized water | qs 100 g |

-continued (d) Lotion:

| | |
|---|---|
| Compound of Example 2 | 0.100 g |
| Polyethylene glycol (PEG 400) | 69.900 g |
| 95% ethanol | 30.000 g |

(e) Hydrophobic ointment:

| | |
|---|---|
| Compound of Example 4 | 0.300 g |
| Isopropyl myristate | 36.400 g |
| Silicone oil ("Rhodorsil 47 V 300" marketed by Rhône-Poulenc) | 36.400 g |
| Beeswax | 13.600 g |
| Silicone oil ("Abil 300 000 cst" marketed by Goldschmidt) | qs 100 g |

(f) Nonionic oil-in-water cream:

| | |
|---|---|
| Compound of Example 6 | 1.000 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the following structural formula (I):

[Structure of formula (I)]

in which:
R1 is an —OH radical, a radical OR7 or a radical —NR8R9, wherein R7, R8 and R9 are as defined below;
R2 is a hydrogen atom, a fluorine atom, a chlorine atom, an alkyl radical having 1 to 3 carbon atoms, an —OH radical or a radical —OR10, wherein R10 is as defined below;
R3 is a hydrogen atom, a methyl radical, an ethyl radical, an isopropyl radical, a tert-butyl radical or a —CF3 radical;
R4 is a hydrogen atom, a fluorine atom, a chlorine atom, a radical —OR11, a methyl radical, an ethyl radical, an isopropyl radical, a tert-butyl radical or a —CF3 radical, wherein R11 is as defined below;
R5 and R6, which may be identical or different, are each a hydrogen atom, a methyl radical, an ethyl radical, an n-propyl radical, an isopropyl radical, a tert-butyl radical, a radical —COR12 or may together form, with the nitrogen atom from which they depend, a piperidine, pyrrolidine, morpholine, pyrrolidin-2-one or piperid-2-one heterocycle, which may be unsubstituted or substituted with one or more methyl, ethyl, fluorine or chlorine groups, wherein R12 is as defined below;
Q is an —OH radical, a radical —OR13, a radical —NR14R15 or a radical —SO2R16, wherein R13, R14, R15 and R16 are as defined below;

[Structure: X—Y divalent radical]

is a divalent radical having the following structure:

a) [acetamide structure]
b) [CH2CH2O structure]
c) [CH2CH2S structure]
d) [CH2CH2N(R17) structure]
e) [CH2CH2CH2 structure]
f) [CH=CH-O structure]

wherein R17 is as defined below;
R7 is a linear or branched alkyl radical having from 1 to 20 carbon atoms, an alkenyl radical, a monohydroxyalkyl radical, a polyhydroxyalkyl radical, an aryl radical, an optionally substituted aralkyl radical or a sugar residue;
R8 and R9, which may be identical or different, are each a hydrogen atom, an —OH radical, an alkyl radical having 1 to 6 carbon atoms, a monohydroxyalkyl radical, a polyhydroxyalkyl radical, an optionally substituted aryl radical, or form with the nitrogen atom from which they depend, an amino acid residue or a peptide residue, or alternatively R8 and R9 may together form, a piperidine, pyrrolidine, morpholine, pyrrolidin-2-one or piperid-2-one heterocycle;
R10 is an alkyl radical having from 1 to 6 carbon atoms;
R11 is an alkyl radical having from 1 to 6 carbon atoms or a mono- or polyether radical;
R12 is an alkyl radical having from 1 to 6 carbon atoms or a radical —OR18, wherein R18 is as defined below;
R13 is a linear or branched alkyl radical having from 1 to 15 carbon atoms;
R14 and R15, which may be identical or different, are each a hydrogen atom, an alkyl radical having from 1 to 6 carbon atoms or a radical —COR19, wherein R19 is as defined below;
R16 is an alkyl radical having from 1 to 6 carbon atoms;
R17 is a hydrogen atom, an alkyl radical having from 1 to 6 carbon atoms or a —CF3 radical;

R18 is an alkyl radical having from 1 to 6 carbon atoms;

R19 is an alkyl radical having from 1 to 6 carbon atoms; or salt thereof when $R_1$ is an OH function, or isomer thereof.

2. An alkali or alkaline earth metal, or zinc or organic amine salt of a compound as defined by claim 1.

3. A compound as defined by claim 1, comprising at least one alkyl radical substituent having from 1 to 6 carbon atoms and selected from the group consisting of methyl, ethyl, n-propyl, i-propyl, cyclopropyl, isopropyl, n-butyl, i-butyl, t-butyl, n-pentyl and n-hexyl radicals.

4. A compound as defined by claim 1, comprising at least one alkyl radical substituent having from 1 to 15 carbon atoms and selected from the group consisting of methyl, ethyl, propyl, isopropyl, cyclopropyl, n-butyl, i-butyl, t-butyl, n-pentyl, n-hexyl, 2-ethylhexyl, octyl and dodecyl radicals.

5. A compound as defined by claim 1, comprising at least one alkyl radical substituent having from 1 to 20 carbon atoms and selected from the group consisting of methyl, ethyl, propyl, isopropyl, cyclopropyl, n-butyl, i-butyl, t-butyl, n-pentyl, n-hexyl, 2-ethylhexyl, octyl, dodecyl, hexadecyl and octadecyl radicals.

6. A compound as defined by claim 1, comprising at least one monohydroxyalkyl radical selected from the group consisting of hydroxymethyl, 2-hydroxyethyl, 2-hydroxypropyl and 3-hydroxypropyl radicals.

7. A compound as defined by claim 1, comprising at least one polyhydroxyalkyl radical selected from the group consisting of 2,3-dihydroxypropyl, 2,3,4-trihydroxybutyl and 2,3,4,5-tetrahydroxypentyl radicals, or a pentaerythritol residue.

8. A compound as defined by claim 1, comprising at least one polyether radical selected from the group consisting of methoxymethoxy, methoxyethoxy and methoxyethoxymethoxy radicals.

9. A compound as defined by claim 1, comprising at least one aryl radical selected from the group consisting of a phenyl radical optionally substituted with at least one halogen, an (a lower) alkyl radical having from 1 to 6 carbon atoms, a hydroxyl, a $C_1$-$C_3$ alkoxy radical, a nitro function, a polyether radical or an amino function optionally protected with an acetyl group or optionally substituted with at least one alkyl radical having from 1 to 6 carbon atoms or an alkoxy radical having from 1 to 6 carbon atoms.

10. A compound as defined by claim 1, comprising at least one aralkyl radical selected from the group consisting of a benzyl or phenethyl radical optionally substituted with at least one halogen, an alkyl radical having from 1 to 6 carbon atoms, a hydroxyl, an alkoxy radical having from 1 to 3 carbon atoms, a nitro function, a polyether radical or an amino function optionally protected with an acetyl group or optionally substituted with at least one alkyl radical having from 1 to 6 carbon atoms or an alkoxy radical having from 1 to 6 carbon atoms.

11. A compound as defined by claim 1, comprising at least one alkenyl radical having from 2 to 5 carbon atoms and having one or more sites of ethylenic unsaturation.

12. A compound as defined by claim 1, comprising at least one sugar residue selected from the group consisting of the residue derived from glucose, galactose or mannose, or from glucuronic acid.

13. A compound as defined by claim 1, comprising at least one amino acid residue selected from the group consisting of a residue derived from lysine, from glycine or from aspartic acid.

14. A compound as defined by claim 1, comprising at least one amino acid residue selected from the group consisting of a dipeptide or tripeptide residue resulting from the combination of amino acids.

15. A compound as defined by claim 1, selected from the group consisting of:
 1. 4-[2-(3-tert-Butyl-4-diethylaminophenyl)-2-hydroxyiminoethoxy]benzoic acid;
 2. 4-[2-(3-tert-Butyl-4-diethylaminophenyl)-2-hydroxyiminoethoxy]-2-hydroxybenzoic acid;
 3. 4-[2-(3-tert-Butyl-4-pyrrolidin-1-ylphenyl)-2-hydroxyiminoethoxy]benzoic acid;
 4. 4-[2-(3-tert-Butyl-4-pyrrolidin-1-ylphenyl)-2-hydroxyiminoethoxy]-2-hydroxybenzoic acid;
 5. 4-{2-[4-(Acetylethylamino)-3-tert-butylphenyl]-2-hydroxyiminoethoxy}benzoic acid;
 6. 4-{2-[4-(Acetylethylamino)-3-tert-butylphenyl]-2-hydroxyiminoethoxy}-2-hydroxybenzoic acid;
 7. Ethyl 4-[2-(3-tert-butyl-4-diethylaminophenyl)-2-hydroxyiminoethoxy]-2-hydroxybenzoate;
 8. Isopropyl 4-[2-(3-tert-butyl-4-diethylaminophenyl)-2-hydroxyiminoethoxy]-2-hydroxybenzoate;
 9. Isobutyl 4-[2-(3-tert-butyl-4-diethylaminophenyl)-2-hydroxyiminoethoxy]-2-hydroxybenzoate;
 10. Octyl 4-[2-(3-tert-butyl-4-diethylaminophenyl)-2-hydroxyiminoethoxy]-2-hydroxybenzoate;
 11. Dodecyl 4-[2-(3-tert-butyl-4-diethylaminophenyl)-2-hydroxyiminoethoxy]-2-hydroxybenzoate;
 12. 4-[2-(3-tert-Butyl-4-diethylaminophenyl)-2-hydroxyiminoethoxy]-N-ethyl -2-hydroxy-N-methylbenzamide;
 13. 4-[2-(3-tert-Butyl-4-diethylaminophenyl)-2-methoxyiminoethoxy]-2-hydroxybenzonic acid;
 14. 4-[2-(3-tert-Butyl-4-diethylaminophenyl)-2-methylhydrazono)ethoxy]-2-hydroxybenzoic acid;
 15. 4-[2-(3-tert-Butyl-4-diethylaminophenyl)-2-pentylhydrazono)ethoxy]-2-hydroxybenzoic acid;
 16. 4-[2-(3-tert-Butyl-4-diethylaminophenyl)-2-2-methanesulfonyliminoethoxy]-2-hydroxybenzoic acid;
 17. 4-[2-(3-tert-Butyl-4-diethylaminophenyl)-2-(pentane-1-sulfonylimino)ethoxy]-2-hydroxybenzoic acid;
 18. 4-[2-(3-tert-Butyl-5-chloro-4-diethylaminophenyl)-2-hydroxyiminoethoxy]-2-hydroxybenzoic acid;
 19. 4-[2-(3-tert-Butyl-4-diethylamino-5-fluorophenyl)-2-hydroxyiminoethoxy]-2-hydroxybenzoic acid;
 20. 4-[2-(3-tert-Butyl-4-diethylamino-5-trifluoromethylphenyl)-2-hydroxyiminoethoxy]-2-hydroxybenzoic acid;
 21. 4-[2-(3-tert-Butyl-4-diethylamino-5-methylphenyl)-2-hydroxyiminoethoxy]-2-hydroxybenzoic acid;
 22. 4-[2-(3-tert-Butyl-4-diethylamino-5-ethylphenyl)-2-hydroxyiminoethoxy]-2-hydroxybenzoic acid;
 23. 4-{2-[3-tert-Butyl-4-diethylamino-5-(2-ethoxyethoxy)phenyl]-2-hydroxyiminoethoxy}-2-hydroxybenzoic acid;
 24. 4-[2-(3-tert-Butyl-4-diethylamino-5-propoxyphenyl)-2-hydroxyiminoethoxy]-2-hydroxybenzoic acid;
 25. 4-[2-(4-diethylamino-3-isopropylphenyl)-2-hydroxyiminoethoxy]-2-hydroxybenzoic acid;
 26. 4-[2-(4-diethylamino-3-trifluoromethylphenyl)-2-hydroxyiminoethoxy]-2-hydroxybenzoic acid;
 27. 4-[2-(4-diethylaminophenyl)-2-hydroxyiminoethoxy]-2-hydroxybenzoic acid;
 28. 4-{2-[3-tert-Butyl-4-(ethylmethylamino)phenyl]-2-hydroxyiminoethoxy}-2-hydroxybenzoic acid;
 29. 4-[2-(3-tert-Butyl-4-dimethylaminophenyl)-2-hydroxyiminoethoxy]-2-hydroxybenzoic acid;

30. 4-{2-[3-tert-Butyl-4-(ethylisobutylamino)phenyl]-2-hydroxyiminoethoxy}-2-hydroxybenzoic acid;

31. 4-[2-(3-tert-Butyl-4-morpholin-4-ylphenyl)-2-hydroxyiminoethoxy]-2-hydroxybenzoic acid;

32. 4-[2-(3-tert-Butyl-4-piperid-1-ylphenyl)-2-hydroxyiminoethoxy]-2-hydroxybenzoic acid;

33. 4-{2-[3-tert-Butyl-4-(2-oxopiperid-1-yl)phenyl]-2-hydroxyiminoethoxy}benzoic acid;

34. 4-{2-[3-tert-Butyl-4-(2-oxopyrrolidin-1-yl)phenyl]-2-hydroxyiminoethoxy}benzoic acid;

35. 4-[2-(3-tert-Butyl-4-ethylaminophenyl)-2-hydroxyiminoethoxy]-2-hydroxybenzoic acid;

36. 4-{2-[4-(Ethylpropionylamino)-3-tert-butylphenyl]-2-hydroxyiminoethoxy}-2-hydroxybenzoic acid;

37. 4-{2-[3-tert-Butyl-4-(ethoxycarbonylethylamino)phenyl]-2-hydroxyiminoethoxy}-2-hydroxybenzoic acid;

38. 4-{2-[3-tert-Butyl-4-(ethylmethoxycarbonylamino)phenyl]-2-hydroxyiminoethoxy}-2-hydroxybenzoic acid;

39. 4-{2-[4-(Ethyltrifluoroacetylamino)-3-tert-butylphenyl]-2-hydroxyiminoethoxy}-2-hydroxybenzoic acid;

40. 4-{2-[4-(Trifluoroacetylamino)-3-tert-butylphenyl]-2-hydroxyiminoethoxy}-2-hydroxybenzoic acid; and 41. 4-{2-[3-tert-Butyl-4-(ethylisopropylamino)phenyl]-2-hydroxyiminoethoxy}-2-hydroxybenzoic acid.

16. A compound as defined by claim 1, wherein:

R1 is a radical —OR7;

R2 is a hydrogen or —OH;

R5 and R6, which may be identical or different, are each a methyl radical or an ethyl radical, or together form with the nitrogen atom from which they depend, a pyrrolidine heterocycle;

Q is a radical —OR13.

17. A pharmaceutical composition comprising a pharmaceutically effective amount of at least one compound (I) as defined by claim 1, formulated into a physiologically acceptable support therefor.

18. The pharmaceutical composition as defined by claim 17, comprising from 0.001% to 10% by weight of said at least one compound (I).

19. The pharmaceutical composition as defined by claim 17, comprising from 0.01% to 1% by weight of said at least one compound (I).

20. A cosmetic composition comprising a cosmetically effective amount of at least one compound (I) as defined by claim 1, formulated into a physiologically acceptable support therefor.

21. The cosmetic composition as defined by claim 20, comprising from 0.001% to 3% by weight of said at least one compound (I).

* * * * *